(12) United States Patent
Jang et al.

(10) Patent No.: US 9,329,095 B2
(45) Date of Patent: May 3, 2016

(54) METHOD FOR EVALUATING PRESTRESSING FORCE OF BONDED TENDON USING VELOCITY OF STRESS WAVES CAUSED BY IMPACT

(75) Inventors: Jung-Bum Jang, Daejeon-si (KR); Byeong-Hwa Kim, Changwon-si (KR); Hong-Pyo Lee, Daejeon-si (KR)

(73) Assignee: Korea Electric Power Corporation, Seoul (KR)

( * ) Notice: Subject to any disclaimer, the term of this patent is extended or adjusted under 35 U.S.C. 154(b) by 92 days.

(21) Appl. No.: 14/348,455

(22) PCT Filed: Jun. 8, 2012

(86) PCT No.: PCT/KR2012/004485
§ 371 (c)(1),
(2), (4) Date: Mar. 28, 2014

(87) PCT Pub. No.: WO2013/047977
PCT Pub. Date: Apr. 4, 2013

(65) Prior Publication Data
US 2014/0238150 A1    Aug. 28, 2014

(30) Foreign Application Priority Data
Sep. 29, 2011 (KR) .................. 10-2011-0098744

(51) Int. Cl.
*G01L 1/04* (2006.01)
*G01L 5/04* (2006.01)
*G01N 29/04* (2006.01)

(52) U.S. Cl.
CPC . *G01L 5/04* (2013.01); *G01L 5/042* (2013.01); *G01N 29/045* (2013.01); *G01N 2291/011* (2013.01); *G01N 2291/02827* (2013.01); *G01N 2291/0421* (2013.01)

(58) Field of Classification Search
CPC ......... G01L 5/04; G01L 5/042; G01N 29/045
USPC ................................ 73/12.04, 12.09, 862.451
See application file for complete search history.

(56) References Cited

U.S. PATENT DOCUMENTS

| 4,322,880 A * | 4/1982 | Lampe | B23P 15/22 220/586 |
| 5,544,210 A * | 8/1996 | Wedellsborg | G21C 13/08 220/586 |
| 2003/0099518 A1 * | 5/2003 | Barley | E02D 29/0233 405/259.1 |

FOREIGN PATENT DOCUMENTS

| KR | 10-2007-0045624 A | 5/2007 |
| KR | 10-2011-0050847 A | 5/2011 |

OTHER PUBLICATIONS

Jang et al., "Development of Nondestructive Assessment Techniques for Prestressed Force of Bonded Tendon," Journal Korean Society of Steel Construction, vol. 23, No. 1, Feb. 2011, with English abstract, pp. 9-12.
Jang et al., "A Sensitivity Analysis of the Key Parameters for the Prediction of the Prestress Force on Bonded Tendons," Nuclear Engineering and Technology, vol. 42, No. 3, Jun. 2010, pp. 319-328.
International Search Report issued in International Application PCT/KR2012/004485 mailed Dec. 14, 2012, with English translation.

* cited by examiner

*Primary Examiner* — Max Noori
(74) *Attorney, Agent, or Firm* — McDermott Will & Emery LLP

(57) ABSTRACT

There is provided a method for evaluating prestressing force of a bonded tendon. The method includes: striking a prestressing strand of a bonded tendon with an impact hammer; measuring an acceleration response signal from the prestressing strand using an accelerometer, and receiving the acceleration response signal with a data logger; and calculating stress wave velocity based on the acceleration response signal received by the data logger, and evaluating prestressing force of the bonded tendon, based on the calculated stress wave velocity, using a controller.

3 Claims, 7 Drawing Sheets

METHOD FOR EVALUATING PRESTRESSING FORCE OF BONDED TENDON USING VELOCITY OF STRESS WAVES CAUSED BY IMPACT

RELATED APPLICATIONS

This application is the U.S. National Phase under 35 U.S.C. §371 of International Application No. PCT/KR2012/004485, filed on Jun. 8, 2012, which in turn claims the benefit of Korean Application No. 10-2011-0098744, filed on Sep. 29, 2011, the disclosures of which are incorporated by reference herein.

TECHNICAL FIELD

The present disclosure relates to a method for evaluating prestressing force of a bonded tendon, and more particularly, to a method for evaluating prestressing force of a bonded tendon using the velocity of stress waves caused by an impact.

BACKGROUND ART

Bonded tendons have been used in heavy-water reactor containment buildings and some light-water reactor containment buildings in Korean nuclear power plants, and evaluation of prestressing forces of the bonded tendons is important for evaluating the structural integrity of the containment buildings. In Korean Wolsug Nuclear Power Plant units 1 to 4 and Uljin Nuclear Power Plant units 1 and 2, bonded tendons have been used in a method of filling the insides of sheathing pipes surrounding the bonded tendons with cement grout.

Particularly, prestressing forces of bonded tendons of a heavy-water reactor type nuclear power plant are indirectly evaluated during reactor operations, by performing a bending test, a destructive test, and a lift-off test using test beams manufactured at the time of nuclear power plant construction. However, since such an indirect evaluation method is ineffective in terms of reliability and economic aspects, the development of direct and practicable methods of estimating prestressing forces of bonded tendons is urgently required.

Methods for estimating prestressing forces of bonded tendons have not been researched, and published methods for estimating prestressing forces of tendons are mainly for unbounded tendons. In addition, most major domestic (Korean) bridges have been constructed using bonded tendons, and evaluation of load bearing capacities and remaining life span of these bridges is an important pending issue. In evaluations of the load bearing capacities and remaining life span of bridges, prestressing forces of bonded tendons are important factors. Therefore, the development of technology for estimating prestressing forces of bonded tendons is considered to be a very urgent and important task.

DISCLOSURE

Technical Problem

An aspect of the present disclosure may provide a method for precisely evaluating prestressing force of a bonded tendon, such as a bonded tendon disposed in a containment building of a nuclear power plant or a bridge, using the velocity of stress waves in the bonded tendon.

Technical Solution

According to an aspect of the present disclosure, a method for evaluating prestressing force of a bonded tendon may include: striking a prestressing strand of a bonded tendon with an impact hammer; measuring an acceleration response signal from the prestressing strand using an accelerometer, and receiving the acceleration response signal with a data logger; and calculating stress wave velocity based on the acceleration response signal received by the data logger, and evaluating prestressing force of the bonded tendon, based on the calculated stress wave velocity, using a controller.

The controller may evaluate the prestressing force of the bonded tendon, based on the acceleration response signal using a system identification algorithm.

In the calculating of the stress wave velocity and evaluating of the prestressing force, the prestressing force of the bonded tendon may be evaluated based on the acceleration response signal using the following formula:

$$V\sqrt{\frac{\rho_c}{\sigma_c}} = k_1\left(\frac{\sigma}{\sigma_s}\right)\left\{k_2 + \frac{1-k_2}{\left[1+\left(k_3\frac{\sigma}{\sigma_s}\right)^{k_4}\right]^{1/k_4}}\right\} + k_5 \quad \text{[Formula]}$$

where V is the stress wave velocity of acceleration response signal, $\rho_c$ is density of concrete, $\sigma_c$ is compressive strength of concrete, $\sigma$ is prestressing stress of the bonded tendon, $\sigma_s$ is tensile strength of steel wires, and $k_1, k_2, k_3, k_4,$ and $k_5$ are constants.

The controller may correct the prestressing force by correcting the acceleration response signal according to atmospheric temperature.

Advantageous Effects

According to embodiments of the present disclosure, the safety of a structure may be evaluated in a very reliable manner. In addition, according to the embodiments of the present disclosure, the prestressing force of a bonded tendon may be directly measured to precisely predict the life span of a structure.

BEST MODE

Figure 1:
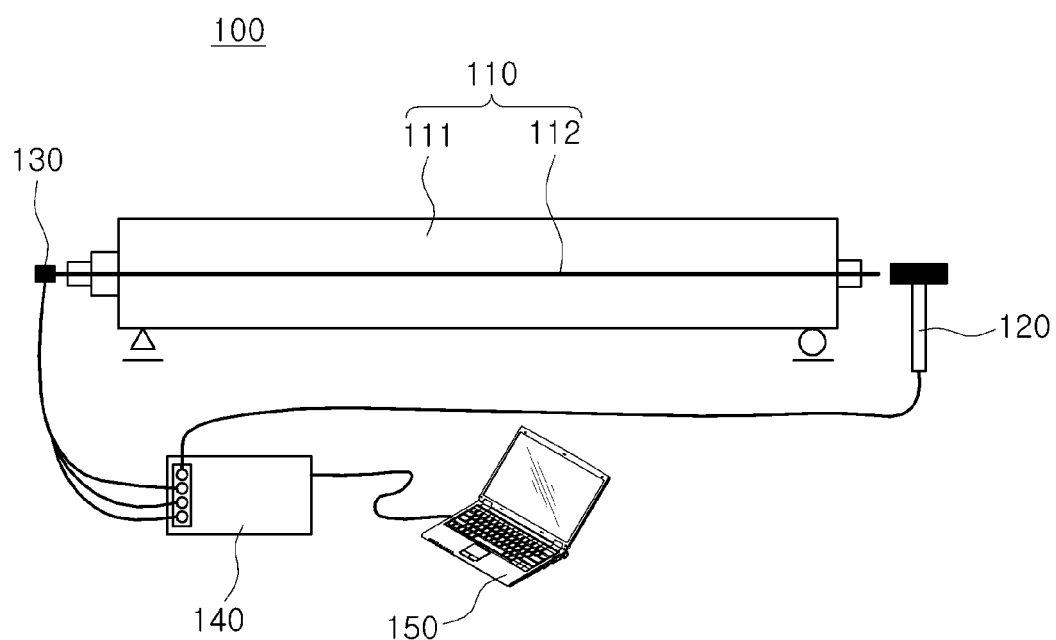
FIG. 1 is a schematic view illustrating an evaluation apparatus used in a method for evaluating prestressing force of a bonded tendon according to an exemplary embodiment of the present disclosure.

FIG. 1 is a schematic view illustrating an evaluation apparatus 100 used in a method for evaluating prestressing force of a bonded tendon according to an exemplary embodiment of the present disclosure.

Referring to FIG. 1, the evaluation apparatus 100 for evaluating prestressing force of a bonded tendon may include an impact hammer 120 configured to strike a bonded tendon 110. The impact hammer 120 may strike a prestressing strand 112 of the bonded tendon 110.

The evaluation apparatus 100 may include an accelerometer 130 attached to the prestressing strand 112 of the bonded tendon 110. The accelerometer 130 may measure an acceleration response signal generated in the prestressing strand 112. The accelerometer 130 may include a load cell. For illustrative purposes, the following description will be mainly given for the case in which the accelerometer 130 includes a load cell.

The evaluation apparatus 100 may include a data logger 140 connected to the accelerometer 130 to receive acceleration response signals measured by the accelerometer 130. The evaluation apparatus 100 may include a controller 150 configured to calculate stress wave velocity based on an acceleration response signal received at the data logger 140 and evaluate prestressing force of the bonded tendon 110 based on the calculated stress wave velocity.

Operations of the evaluation apparatus 100 will now be described according to an exemplary embodiment of the present disclosure.

1. First and Second Operations 8 m long rectangular specimens and 20 m long rectangular specimens may be prepared to evaluate prestressing forces of bonded tendons.

Specifications and test methods for the specimens are as follows.

A. 8-m Specimens

Figure 2:
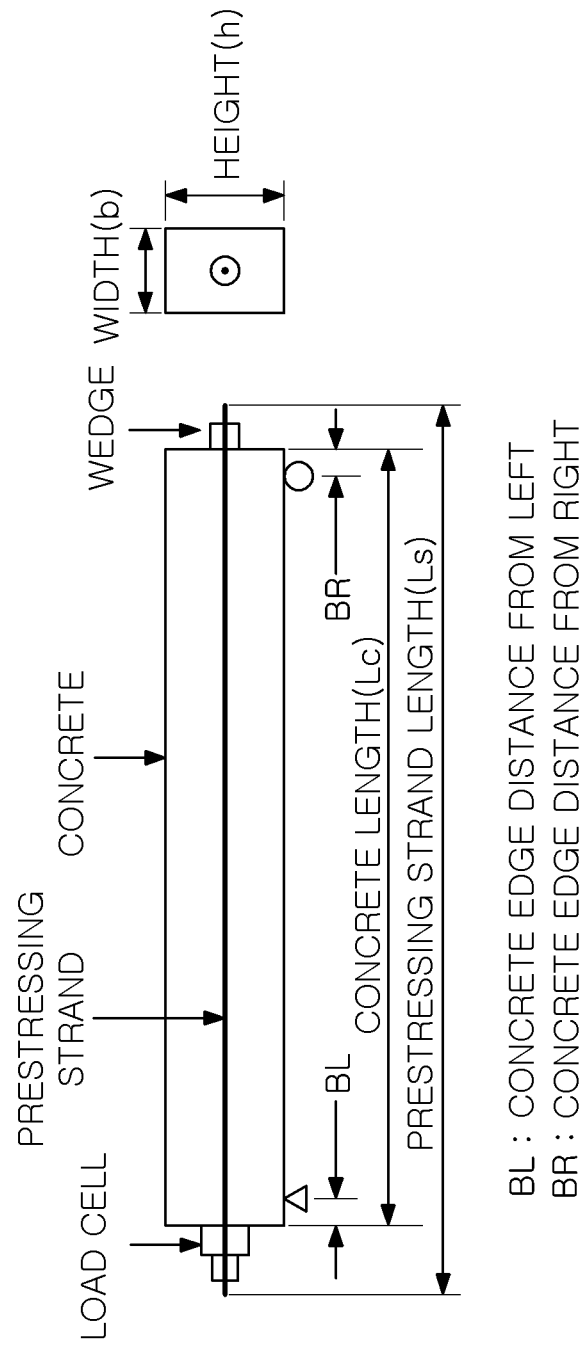
FIG. 2 is a view illustrating an 8-m specimen according to an exemplary embodiment of the present disclosure.

Referring to FIG. 2, strands (Manufactured according to Korean industrial standard KSD 7002 SWPC 7B) having a standard diameter of 15.2 mm, a nominal cross-sectional area of 138.7 mm$^2$, a maximum tensile load Tu=260.68 kN may be used as prestressing strands 112 of the 8-m specimens. Each of the prestressing strands 112 may be linearly disposed through the center of a cross-section of concrete 111 to simulate a prestressing system of a containment building of a nuclear power plant. Bonded tendons 110 may be prepared by filling sheathing pipes with cement grout after prestressing the prestressing strands 112. A load cell may be attached to each of the specimens for measuring initial prestressing force. Final initial prestressing forces of the prestressing strands 112 prestressed at sides opposite to the load cells are shown in Table 1 below.

The concept of an impact test for measuring the velocity of a stress wave according to the prestressing force of a bonded tendon is shown in FIG. 1. The impact hammer 120 (a 086C04 model by PCB) is used to longitudinally strike the prestressing strand 112. The accelerometer 130 (a 352B10 model by PCB) is used to measure a longitudinal vibration response signal, and a CRIO 9073 and a 4-channel NI 9233 by NI are used together as the data logger 140. Two 12-V automotive batteries connected in series are used as a power source of the data logger 140 for preventing power source noise from affecting a response signal, and the controller 150 uses an independent power source.

In this test, an impact test is performed on each specimen 160 or more times after attaching three accelerometers 130 to ends of three core steel wires of a prestressing strand opposite to an end of the prestressing strand to be impacted.

Figure 3:
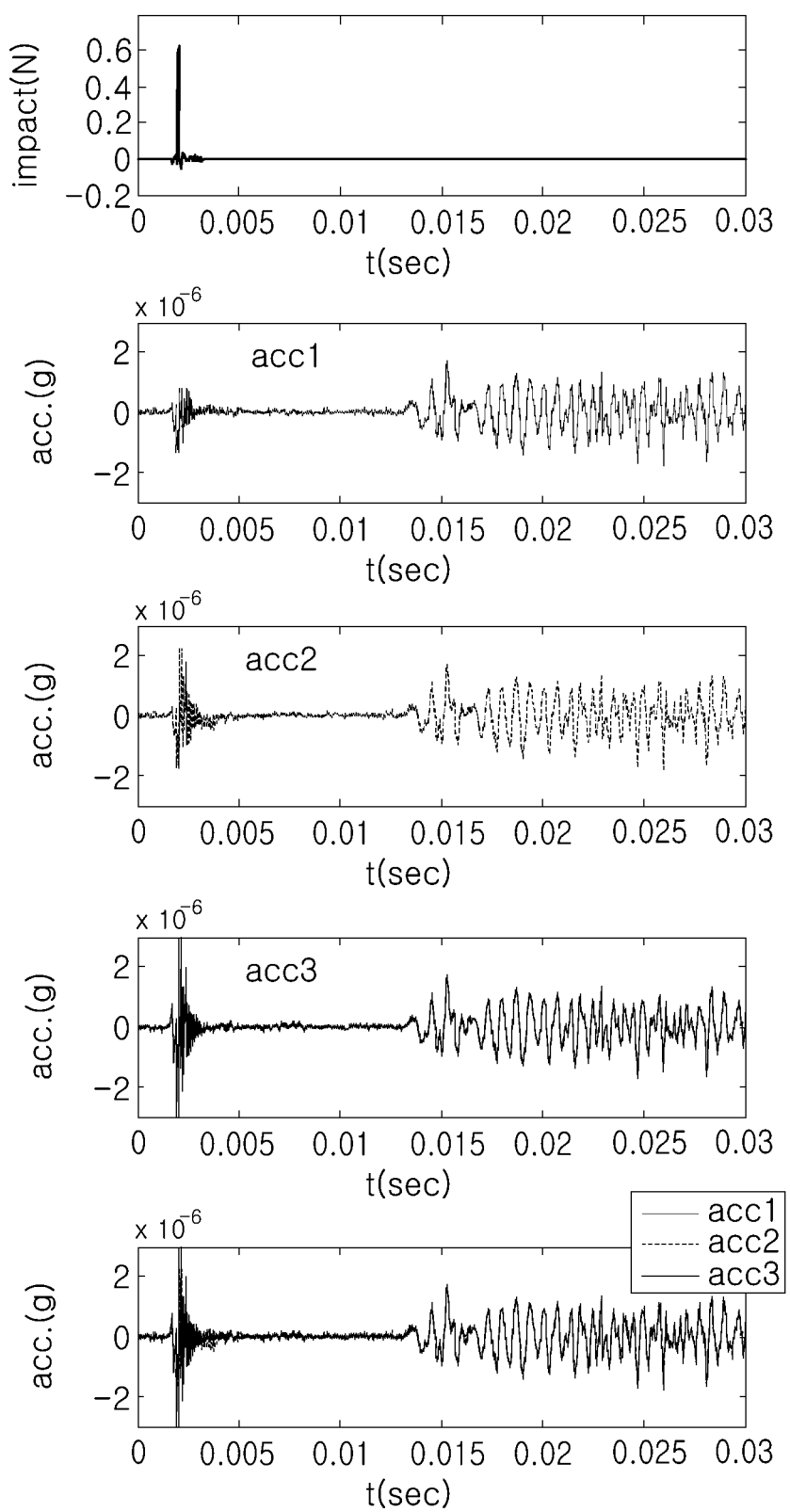
FIG. 3 is a view illustrating acceleration response signals measured from a specimen according to an exemplary embodiment of the present disclosure.

Referring to FIG. 3, acceleration response signals measured from the specimens are shown.

Figure 4:
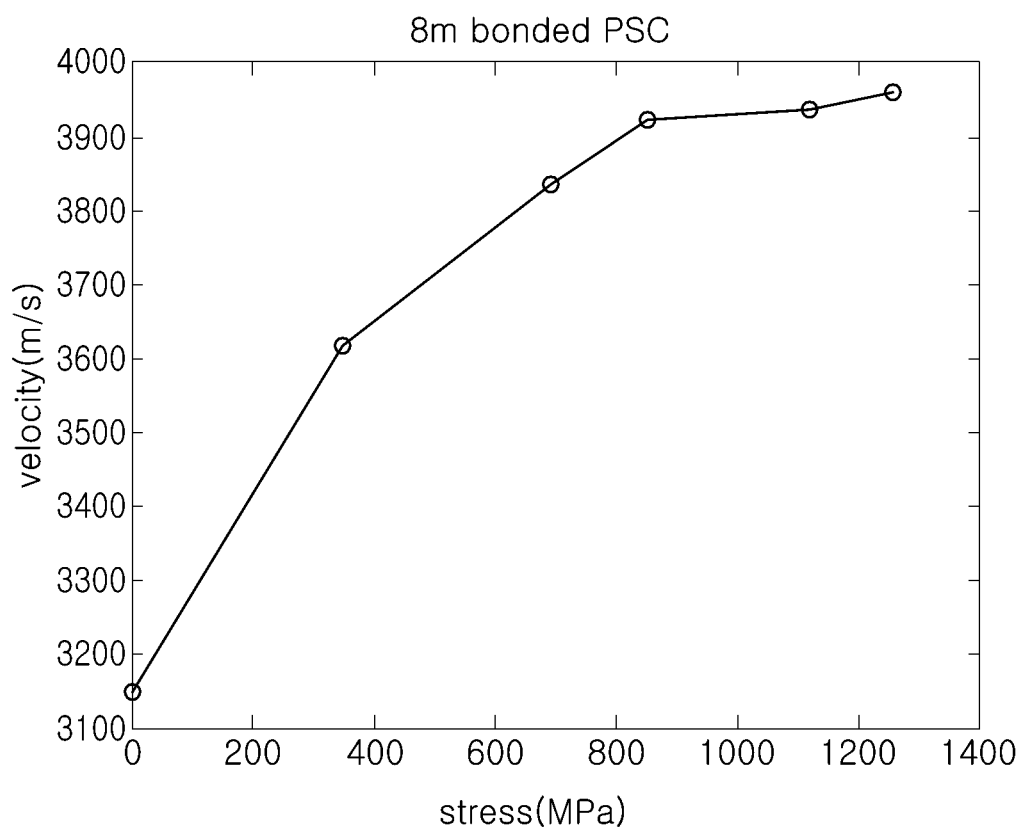
FIG. 4 is a view illustrating a relationship between stress wave velocity and prestressing force, according to an exemplary embodiment of the present disclosure.

The stress wave velocity measured from each specimen in the impact test is shown in Table 2, and a relationship between the stress wave velocity and prestressing force is shown in FIG. 4.

TABLE 2

Results of impact test (8-m specimen)

| Specimens | 8-m specimens | | | |
|---|---|---|---|---|
| | Prestressing stress σ (Mpa) | Length L (m) | Propagation time t (×10$^{-3}$ sec) | Stress wave velocity V (m/s) |
| No. 1 | 10.0 | 8.278 | 2.6306 | 3147.0 |
| No. 2 | 342.7 | 8.439 | 2.3343 | 3615.6 |
| No. 3 | 656.1 | 8.444 | 2.2024 | 3834.2 |
| No. 4 | 783.2 | 8.433 | 2.1537 | 3916.0 |
| No. 5 | 1071.9 | 8.435 | 2.1447 | 3933.5 |
| No. 6 | 1203.4 | 8.433 | 2.1314 | 3956.8 |
| Average temperature (° C.) | | 25 | | |

B. 20-m Specimens 20-m specimens may be prepared as shown in Table 3 in the same manner as that used to prepare the 8-m specimens. An impact test may be performed in the same manner as that explained in section (A), and test results shown in Table 4 may be obtained.

TABLE 1

8-m specimens

| | Concrete | | | | Prestressing strands | | |
|---|---|---|---|---|---|---|---|
| Specimens | Length Lc (m) | Width b (m) | Height h (m) | Compressive strength (Mpa) | Length Ls (m) | Initial prestressing force T (kN) | Notes |
| No. 1 | 7.999 | 0.302 | 0.302 | 37.08 | 8.278 | 0.0 | 0 |
| No. 2 | 8.000 | 0.303 | 0.301 | 37.08 | 8.439 | 145.6 | 19% Tu |
| No. 3 | 7.995 | 0.300 | 0.300 | 37.08 | 8.444 | 263.8 | 34% Tu |
| No. 4 | 7.994 | 0.302 | 0.301 | 37.08 | 8.433 | 355.8 | 46% Tu |
| No. 5 | 7.998 | 0.303 | 0.299 | 37.08 | 8.435 | 465.0 | 59% Tu |
| No. 6 | 7.993 | 0.303 | 0.303 | 37.08 | 8.433 | 522.5 | 67% Tu |

TABLE 3

20-m specimens

| Specimens | Concrete Width b (m) | Concrete Height h (m) | Concrete Length Lc | Number of prestressing strands |
|---|---|---|---|---|
| No. 1 | 0.502 | 0.504 | 19.987 | 7 |
| No. 2 | 0.502 | 0.502 | 19.990 | 7 |
| No. 3 | 0.504 | 0.499 | 20.010 | 7 |
| No. 4 | 0.503 | 0.511 | 20.020 | 7 |
| No. 5 | 0.501 | 0.511 | 20.001 | 7 |
| No. 6 | 0.504 | 0.517 | 20.009 | 14 |

TABLE 4

Results of impact test (20-m specimens)

| | 20-m specimens | |
|---|---|---|
| Specimens | Prestressing stress σ (Mpa) | Stress wave velocity V (m/s) |
| No. 1 | 10.7 | 3627.1 |
| No. 2 | 631.5 | 3836.3 |
| No. 3 | 828.5 | 3942.6 |
| No. 4 | 966.1 | 3924.1 |
| No. 5 | 1218.1 | 3958.5 |
| No. 6 | 873.8 | 4034.3 |
| Average temperature(° C.) | 9.1 | |

2. Temperature Compensation

Figure 5:
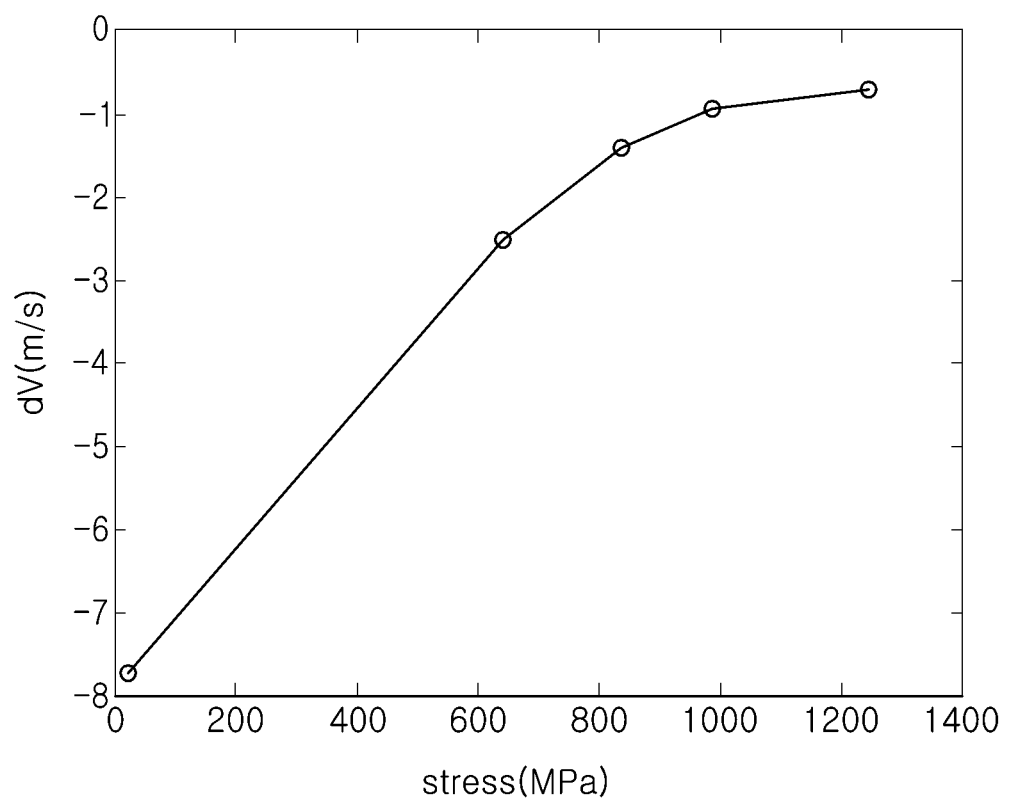
FIG. 5 is a view illustrating a stress wave velocity correction curve for unit temperature difference $\Delta T$ (1° C.) for 20-m specimens according to an exemplary embodiment of the present disclosure.

Referring to the results of the impact tests, as temperature is increased, the prestressing force of the bonded tendon 110 is increased but the stress wave velocity in the bonded tendon 110 is decreased. That is, atmospheric temperature affects the prestressing force of the bonded tendon 110. To reflect this in an evaluation formula, a temperature compensation curve for each unit temperature increase ΔT=1° C. may be obtained from the measured results using cubic interpolation as shown in FIG. 5. The stress wave velocity values measured in the impact test performed on the 20-m specimens at atmospheric temperature of 9.1° C. (Table 4) may be revised based on atmospheric temperature of 25° C. as shown in Table 5.

In FIG. 5, dV (deviation velocity) denotes a velocity compensation value per unit temperature difference. After calculating a velocity compensation value for a difference between a measured temperature and a reference temperature (25° C.) based on dV, the calculated velocity compensation value may be added to or subtracted from a measured stress wave velocity value to obtain stress wave velocity value at the reference temperature.

For example, Specimen No. 1 has a stress wave velocity value of 3627.1 m/s before compensation as shown in Table 4 (9.1° C.) and a stress wave velocity value of 3501.7 m/s after compensation as shown in Table 5 (25° C.).

In detail, the temperature difference of 15.9° C. (25° C.−9.1° C.=15.9° C.) is multiplied by a velocity compensation value per unit temperature dV=−7.89 m/s to obtain a velocity compensation value of −125.4 m/s, and the velocity compensation value is added to the non-compensated stress wave velocity value of 3627.1 m/s to obtain the compensated stress wave velocity value of 3501.7 m/s.

The stress wave velocity values of the other specimens may be compensated based on temperature in this manner, and results of compensation are shown in Table 5.

TABLE 5

Test results of 20-m specimens after temperature compensation

| | 20-m specimens | |
|---|---|---|
| Specimens | Prestressing stress σ (Mpa) | Stress wave velocity V (m/s) |
| No. 1 | 10.7 | 3501.7 |
| No. 2 | 631.5 | 3795.1 |
| No. 3 | 828.5 | 3919.8 |
| No. 4 | 966.1 | 3908.4 |
| No. 5 | 1218.1 | 3947.5 |
| Average temperature (° C.) | 25 | |

3. Third Operation

The test results showing the relationship between stress wave velocity and prestressing force of the specimens may be used to estimate the stress of the bonded tendon 110 installed in a real structure based on the law of similarity. As a result, variables affecting the relationship between stress wave velocity and prestressing force of the bonded tendon 110 may be expressed by a dimensionless function as shown in Formula 1 below:

$$V\sqrt{\frac{\rho_c}{\sigma_c}} = f\left(\frac{\sigma}{\sigma_s}\right)$$ [Formula 1]

where V is the stress wave velocity of acceleration response signal, $\rho_c$ is density of concrete, $\sigma_c$ is compressive strength of concrete, σ is prestressing stress of a bonded tendon, $\sigma_s$ is tensile strength of steel wires, and f: function.

Figure 6:
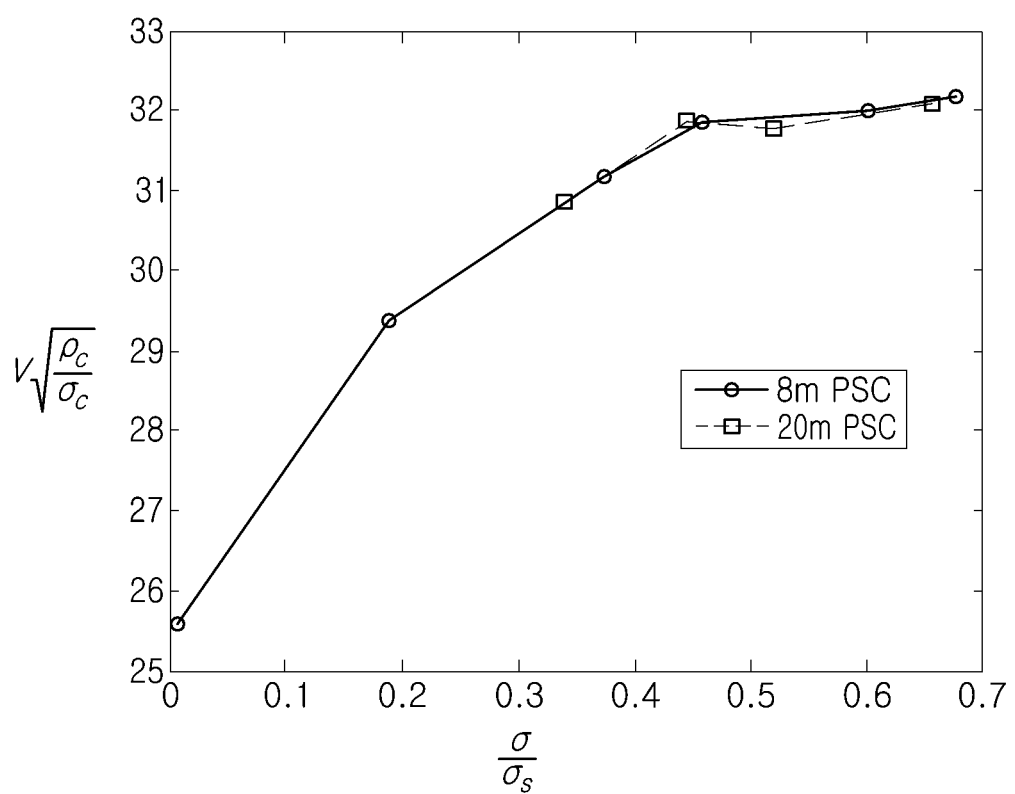
FIG. 6 is a view illustrating a dimensionless relationship between stress wave velocity and prestressing force of a bonded tendon according to an exemplary embodiment of the present disclosure.

The test results of the 8-m specimens shown in Table 2 and the test results of the 20-m specimens shown in Table 5 are related according to the dimensionless function as shown in FIG. 6 and Tables 6 and 7.

TABLE 6

Dimensionless relationship between prestressing force and stress wave velocity of bonded tendon-8 m

| Specimens | $\dfrac{\sigma}{\sigma_s}$ | $V\sqrt{\dfrac{\rho_c}{\sigma_c}}$ |
|---|---|---|
| No. 1 | 0.0054 | 25.5806 |
| No. 2 | 0.1882 | 29.3896 |
| No. 3 | 0.3733 | 31.1665 |
| No. 4 | 0.4590 | 31.8314 |
| No. 5 | 0.6008 | 31.9737 |
| No. 6 | 0.6752 | 32.16311 |

TABLE 7

Dimensionless relationship between prestressing force and stress wave velocity of bonded tendon-20 m

| Specimens | $\dfrac{\sigma}{\sigma_s}$ | $V\sqrt{\dfrac{\rho_c}{\sigma_c}}$ |
|---|---|---|
| No. 2 | 0.3395 | 30.8486 |
| No. 3 | 0.4454 | 31.8623 |
| No. 4 | 0.5194 | 31.7692 |
| No. 5 | 0.6549 | 32.0838 |

Referring to FIG. 6, since the measured pieces of data have a tendency very similar to the Ramberg-Osgood function, curve fitting by Formula 2 may be performed to obtain data in a non-tested region by interpolation and extrapolation.

$$V\sqrt{\frac{\rho_c}{\sigma_c}} = k_1\left(\frac{\sigma}{\sigma_s}\right)\left\{k_2 + \frac{1-k_2}{\left[1+\left(k_3\frac{\sigma}{\sigma_s}\right)^{k_4}\right]^{1/k_4}}\right\} + k_5 \quad \text{[Formula 2]}$$

where V is the stress wave velocity of acceleration response signal, $\rho_c$ is density of concrete, $\sigma_c$ is compressive strength of concrete, $\sigma$ is prestressing stress of a bonded tendon, $\sigma_s$ is tensile strength of steel wires, and $k_1$, $k_2$, $k_3$, $k_4$, and $k_5$ are constants.

Figure 7:
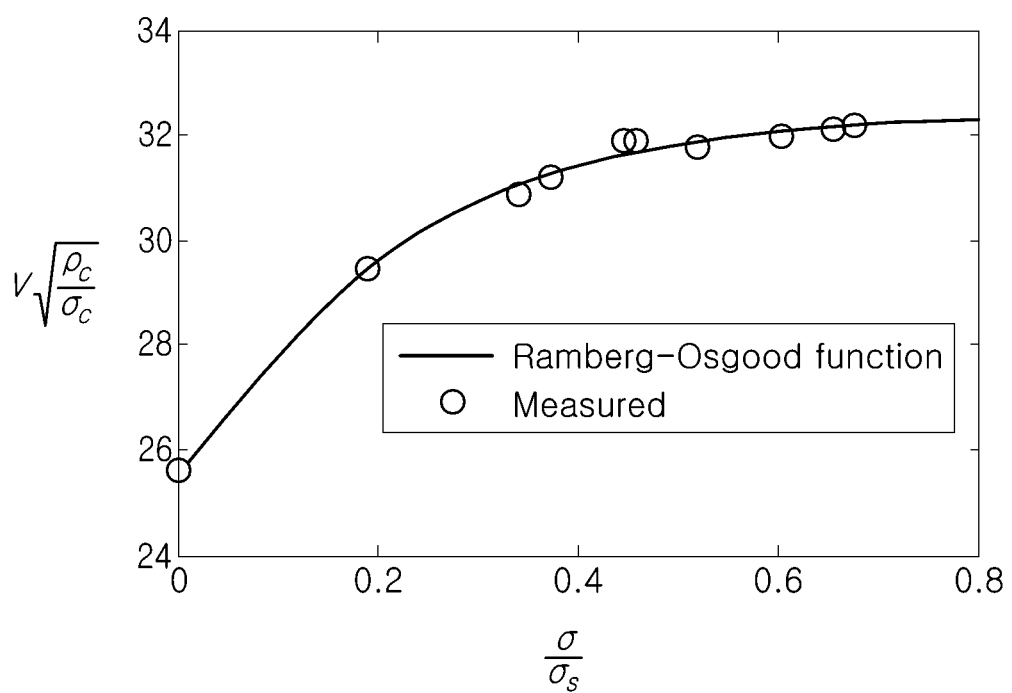
FIG. 7 is a view illustrating a relationship function between stress wave velocity and prestressing force of a bonded tendon according to an exemplary embodiment of the present disclosure.

The unknown constants $k_1$, $k_2$, $k_3$, $k_4$, and $k_5$ in Formula 2 may be estimated by an system identification algorithm as shown in Table 8. Formula 2 (estimation curve formula) and data in Tables 6 and 7 are compared as shown in FIG. 7.

TABLE 8

| Ramberg-Osgood Function coefficients | |
|---|---|
| | Coefficients |
| $k_1$ | 22.8571 |
| $k_2$ | 0.0104 |
| $k_3$ | 3.2916 |
| $k_4$ | 2.5125 |
| $k_5$ | 25.4623 |

The stress wave velocity of the bonded tendon 110 may be measured to evaluate the prestressing force of the bonded tendon 110 using the relationship between the prestressing force and stress wave velocity of the 110 obtained from the above-described tests.

Therefore, the safety of a structure may be reliably evaluated using the method for evaluating prestressing force of a bonded tendon of the present disclosure. In addition, since the prestressing force of a bonded tendon can be directly measured by the method of the present disclosure, the life span of a structure may be precisely predicted.

While exemplary embodiments have been shown and described above, it will be apparent to those skilled in the art that modifications, variations, and equivalents could be made without departing from the spirit and scope of the present disclosure as defined by the appended claims.

The invention claimed is:

1. A method for evaluating prestressing force of a bonded tendon, the method comprising:
   striking a prestressing strand of a bonded tendon with an impact hammer;
   measuring an acceleration response signal from the prestressing strand using an accelerometer, and receiving the acceleration response signal with a data logger; and
   calculating stress wave velocity based on the acceleration response signal received by the data logger, and evaluating prestressing force of the bonded tendon, based on the calculated stress wave velocity, using a controller,
   wherein the prestressing force of the bonded tendon is evaluated based on the acceleration response signal using the following formula:

$$V\sqrt{\frac{\rho_c}{\sigma_c}} = k_1\left(\frac{\sigma}{\sigma_s}\right)\left\{k_2 + \frac{1-k_2}{\left[1+\left(k_3\frac{\sigma}{\sigma_s}\right)^{k_4}\right]^{1/k_4}}\right\} + k_5$$

where V is the stress wave velocity of acceleration response signal,
$\rho_c$ is density of concrete,
$\sigma_c$ is compressive strength of concrete,
$\sigma$ is prestressing stress of the bonded tendon,
$\sigma_s$ is tensile strength of steel wires, and
$k_1$, $k_7$, $k_3$, $k_4$, and $k_5$ are constants.

2. The method of claim 1, wherein the controller evaluates the prestressing force of the bonded tendon, based on the acceleration response signal using a system identification algorithm.

3. A method for evaluating prestressing force of a bonded tendon, the method comprising:
   striking a prestressing strand of a bonded tendon with an impact hammer;
   measuring an acceleration response signal from the prestressing strand using an accelerometer, and receiving the acceleration response signal with a data logger; and
   calculating stress wave velocity based on the acceleration response signal received by the data logger, and evaluating prestressing force of the bonded tendon, based on the calculated stress wave velocity, using a controller,
   wherein the controller corrects the prestressing force by correcting the acceleration response signal according to atmospheric temperature.

* * * * *